United States Patent
Koss et al.

(10) Patent No.: US 6,953,872 B1
(45) Date of Patent: Oct. 11, 2005

(54) PROCESS OF PRODUCING $C_2$ TO $C_4$ OLEFINS FROM A FEED MIXTURE CONTAING $C_4$ TO $C_8$ OLEFINS

(75) Inventors: Ulrich Koss, Darmstadt (DE); Martin Rothaemel, Frankfurt am Main (DE); Peter König, Frankfurt am Main (DE)

(73) Assignee: MG Technologies AG, Frankfurt am Main (DE)

( * ) Notice: Subject to any disclaimer, the term of this patent is extended or adjusted under 35 U.S.C. 154(b) by 512 days.

(21) Appl. No.: 10/030,802

(22) PCT Filed: May 31, 2000

(86) PCT No.: PCT/EP00/04960

§ 371 (c)(1),
(2), (4) Date: May 6, 2002

(87) PCT Pub. No.: WO01/05909

PCT Pub. Date: Jan. 25, 2001

(30) Foreign Application Priority Data

Jul. 15, 1999 (DE) .......................... 199 33 063

(51) Int. Cl.$^7$ .......................... C07C 4/06; C10G 11/00
(52) U.S. Cl. .................. 585/652; 585/650; 585/651; 585/648; 585/653; 208/113; 208/120.01
(58) Field of Search .................. 585/652, 650, 585/651, 648, 653; 208/113, 120.01

(56) References Cited

U.S. PATENT DOCUMENTS 4,743,357 A * 5/1988 Patel et al. ................. 208/113

* cited by examiner

Primary Examiner—Thuan Dinh Dang
(74) Attorney, Agent, or Firm—Norris McLaughlin & Marcus PA

(57) ABSTRACT

This invention relates to a process of producing C2- to C4-olefins from steam and a feed mixture containing C4- to C8-olefins, wherein the feed mixture containing steam is introduced into a reactor with an inlet temperature of 300 to 700° C., said reactor comprising a bed of granular, form-selective zeolite catalyst, and wherein a product mixture containing steam and C2- to C4-olefins is withdrawn from the bed and is passed through at least one cooling means.

5 Claims, 1 Drawing Sheet

PROCESS OF PRODUCING $C_2$ TO $C_4$ OLEFINS FROM A FEED MIXTURE CONTAING $C_4$ TO $C_8$ OLEFINS

This application is a 371 of PCT/EP00/04960 filed on May 31, 2000.

This invention relates to a process of producing $C_2$- to $C_4$-olefins from steam and a feed mixture containing $C_4$- to $C_8$-olefins, wherein the feed mixture containing steam is introduced into a reactor with an inlet temperature of 300 to 700° C., said reactor comprising a bed of granular, form-selective zeolite catalyst, and wherein a product mixture containing steam and $C_2$- to $C_4$-olefins is withdrawn from the bed and is passed through at least one cooling means. Such process is known from DE 196 48 795 A1. It is the object underlying the invention to further develop this process and to operate at costs as reasonable as possible. In accordance with the invention, this is achieved in the above-mentioned process in that the vaporous product mixture coming from the cooling means is pressurized and the pressure of the product mixture is increased by 0.3 to 7 bar, preferably by at least 1 bar, that the pressurized product mixture is passed through an indirect heat exchanger, and the product mixture is cooled therein to such an extent that a water-rich condensate is produced by releasing heat of condensation, that the product mixture containing condensate is introduced into a separator from which a water-rich condensate and, separate therefrom, a vaporous product mixture containing $C_2$- to $C_4$-olefins is withdrawn, that water-rich condensate coming from the separator is expanded and evaporated in the indirect heat exchanger by utilizing the heat of condensation previously released during condensation, that at least part of the steam from the indirect heat exchanger is introduced into a mixing chamber to which the feed mixture containing $C_4$- to $C_8$-olefins is supplied, and that from the mixing chamber a mixture is withdrawn which is heated and introduced into the reactor.

In the process in accordance with the invention, the condensation temperature is increased by increasing the pressure by 0.3 to 7 bar and preferably by at least 1 bar, so that water-rich condensate is obtained already upon cooling to the elevated condensation temperature. The water-rich condensate coming from the separator is expanded by a pressure difference of 0.3 to 7 bar, so that its evaporation temperature decreases below the condensation temperature which had previously been raised by compression. Thus, it is achieved that the amount of heat produced during condensation can directly be reused for evaporating the water-rich condensate.

The mixture of steam and hydrocarbons supplied to the reactor expediently contains these components in a weight ratio of 0.5:1 to 3:1. In the reactor, the granular zeolite catalyst is arranged in the form of a bed. The grain sizes of the catalyst usually lie in the range from 1 to 8 mm. The zeolite is of the pentasil type, it has form-selective properties. In the catalyst, the atomic ratio Si:Al lies in the range from 10:1 to 200:1. The primary crystallites of the alumosilicate preferably have a narrow grain-size distribution with diameters in the range from 0.1 to 0.9 $\mu$m; the BET-surface usually lies in the range from 300 to 600 $m^2/g$, and the pore volume (according to mercury porosimetry) is about 0.3 to 0.8 $cm^3/g$. Alumina trihydrate preferably is used as binder to keep the primary crystallites together.

The feed mixture to be processed, which contains $C_4$- to $C_8$-olefins, may vary in a wide range, it may for instance be light gasoline from a catalytic cracking plant or a raffinate from the product of a steam cracker. The feed mixture may also contain hydrocarbons with more than 8 C-atoms per molecule, with these higher-boiling components preferably being removed, at least in part, before reaching the reactor. The separation need, however, not be performed completely, since longer-chain molecules are not detrimental to the conversion in the reactor, but above all represent superfluous ballast only. If one intends to separate the longer-chain olefins in the mixing chamber, it is recommended to design the mixing chamber as a column with a gas- and liquid-permeable packing and to pass the feed mixture onto the upper portion of the packing. At the same time, a partial amount of the steam is introduced into the lower portion of the packing, this partial amount being selected such that the $C_4$- to $C_8$-olefins from the feed mixture are evaporated and are removed from the column together with the steam. The higher-boiling hydrocarbons remain in the column completely or to a large extent and are withdrawn from the bottom thereof together with water that has formed.

Embodiments of the process will be explained by means of the drawing, wherein.

Figure 1:
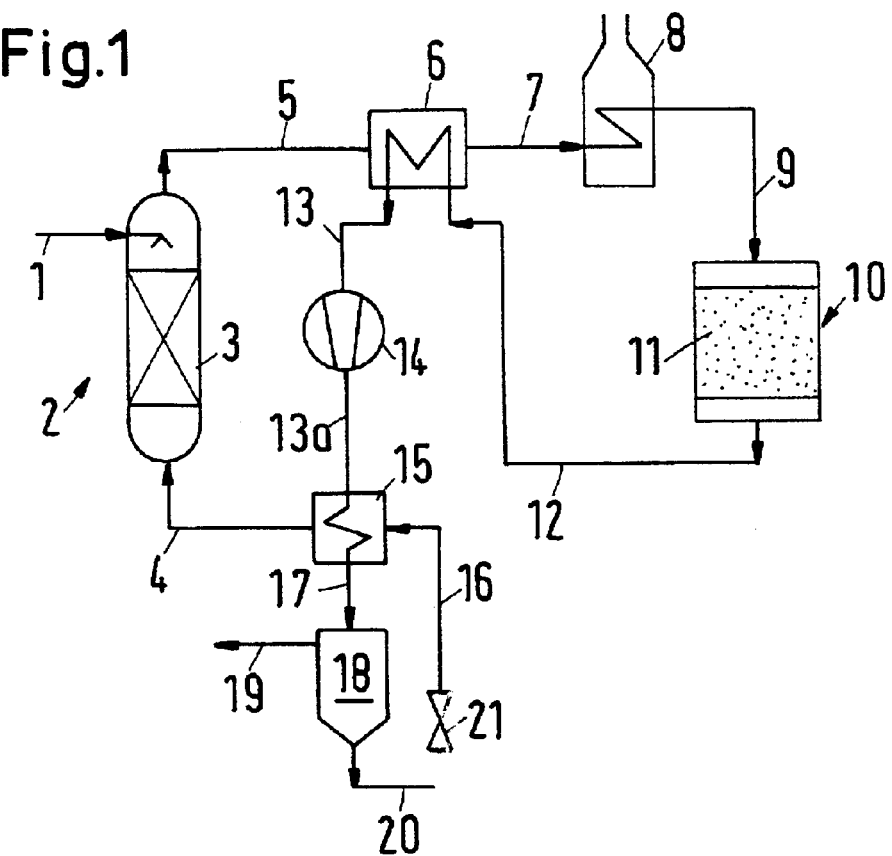
FIG. 1 shows a flow diagram of the process.

In accordance with FIG. 1, the feed mixture containing $C_4$- to $C_8$-olefins is introduced through line (1) into column (2) serving as mixing chamber, which comprises a packing (3) of gas- and liquid-permeable elements, e.g. trays. At the same time, steam is supplied through line (4), which steam enters the packing (3) from below and in so doing evaporates the feed mixture, entraining it to the top of the column (2). The mixture of feed mixture and steam flows through line (5) to a heat exchanger (6) in which the temperature of the mixture is increased. Finally, the mixture flows through line (7) to a heater (8) which may be fired or operated electrically, and leaves the same with a temperature in the range from 300 to 700° C., preferably 400 to 600° C. With this temperature, the mixture is introduced through line (9) into the reactor (10) which contains a bed (11) of a form-selective zeolite catalyst of the pentasil type. The Si:Al atomic ratio of the zeolite lies in the range from 10:1 to 200:1. The composition of the feed mixture which is introduced through line (9) into the reactor (10) may vary, and it is recommended to adjust the content of aromatics, calculated anhydrous, to not more than 20 wt-%, preferably to not more than 10 wt-%. This is recommendable because a higher content of aromatics results in a premature deactivation of the catalyst due to carbon deposits. Furthermore, the feed mixture should expediently be free from components having threefold C—C-bonds or conjugated double bonds, since they likewise deactivate the catalyst.

The conversion in the reactor (10) is effected adiabatically, so that from the bed a product mixture is withdrawn whose temperature is 20 to 80° C. lower than the inlet temperature. The added content of ethylene, propylene and butene isomers in the product mixture withdrawn via line (12) is at least 60 wt-% and preferably at least 70 wt % of the olefinic constituents of the feed mixture. It is recommended to operate the reactor at relatively low pressures in the range from 0.2 to 3 bar. Usually, the pressures in the reactor lie in the range from 0.6 to 1.5 bar.

The product mixture of line (12) releases part of its heat in the heat exchanger (6), and it usually leaves the heat exchanger via line (13) with a temperature in the range from 60 to 200° C. and a pressure in the range from 0.5 to 3 bar. In the compressor (14), the pressure of the vaporous product mixture is increased by 0.3 to 7 bar and mostly by at least 1 bar, with the temperature at which condensate is formed also being increased. Through line (13a) the pressurized mixture flows to the indirect heat exchanger (15). In the heat exchanger (15), intensive cooling is provided, and water-rich condensate from line (16) serves as cooling medium. This condensate evaporates, and the steam formed is introduced through line (4) into the column (2). In the product mixture coming from the compressor (14), water-rich condensate is formed through cooling in the indirect heat exchanger (15). The product mixture is introduced through line (17) into a separator (18), and the desired product containing $C_2$- to $C_4$-olefins is withdrawn therefrom through line (19), which product may also be supplied to a subsequent cleaning not represented here. The water-rich condensate obtained in the separator (18) flows through line (20) first of all to an expansion valve (21) where it is expanded by a pressure difference of 0.3 to 7 bar. The condensate is cooled further, and its evaporation temperature is decreased. The further utilization of this condensate via line (16) has already been explained.

Figure 2:
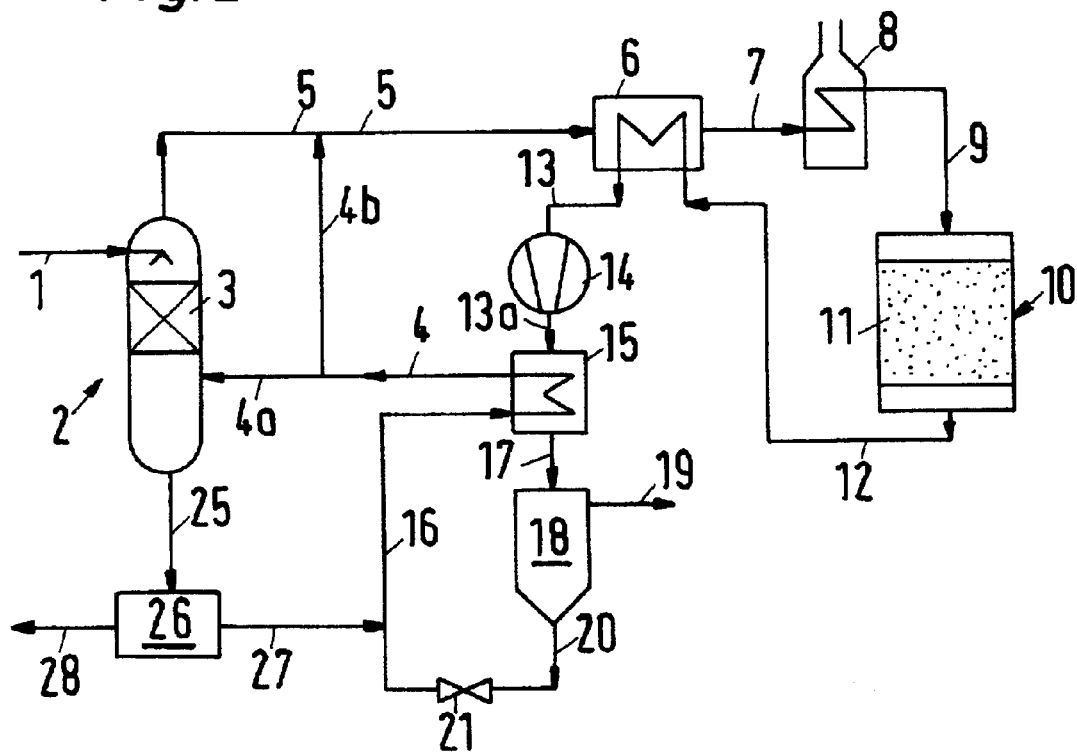
FIG. 2 shows a modification of the process of FIG. 1.

The process variant of FIG. 2 relates to the processing of a feed mixture supplied via line (1), which apart from $C_4$- to $C_8$-olefins also contains higher-boiling components. As far as FIG. 2 uses the same reference numerals as FIG. 1, these have the meaning already explained in connection with FIG. 1. From the indirect heat exchanger (15) steam is withdrawn via line (4) which is divided into lines (4a) and (4b). The amount of steam flowing in line (4a) is sufficient to evaporate the $C_4$- to $C_8$-olefins supplied via line (1) in column (2), but where the higher-boiling hydrocarbons are not evaporated to a large extent and together with water are accumulated as liquid in the bottom of column (2). From there, the liquid mixture is supplied through line (25) to a separator (26), from which the separated water is added to the condensate of line (16) through line (27). The separated hydrocarbons are removed from the process via line (28). To the mixture of steam and $C_2$- to $C_4$-olefins, which is withdrawn from column (2) via line (5), the second partial stream of steam is added, which was branched off via line (4b), and the mixture is first of all supplied to the heat exchanger (6) before the further treatment explained in connection with FIG. 1 is performed.

EXAMPLES

The procedure is as represented in the drawing, where the zeolite catalyst of the pentasil type has an atomic ratio Si:Al of 70. The feed mixture of Example 1 only contains hydrocarbons up to CB, in Example 2 also higher hydrocarbons are processed.

Example 1

In the process in accordance with FIG. 1, 100 000 kg/h of a feed mixture are supplied, whose composition is indicated in Table 1 and which has a temperature of 80° C.:

TABLE 1

|  | Example 1 | Example 2 | A | B |
|---|---|---|---|---|
| Non-cyclic $C_4$- to $C_5$-olefins (wt-%) | 48.0 | 27.0 | 0.2 | 33.0 |
| Non-cyclic $C_{8+}$-olefins (wt-%) | — | 4.0 | 6.8 | 3.0 |
| $C_4$- to $C_8$-paraffins (wt-%) | 38.0 | 13.0 | 0.2 | 23.3 |
| $C_{8+}$-paraffins (wt-%) | — | 5.0 | 9.4 | 3.9 |
| Aromatics (up to $C_8$) (wt-%) | 8.0 | 13.0 | 0.6 | 14.7 |
| Aromatics ($c_{8+}$) (wt-%) | — | 11.0 | 51.7 | 3.2 |
| Cycloalkanes and cycloalkenes up to $C_8$ (wt-%) | 6.0 | 14.0 | 4.3 | 16.3 |
| Cycloalkanes, cykloalkenes, polynaphthenes, $C_{8+}$(wt-%) | — | 7.0 | 26.8 | 2.6 |

By supplying 150000 kg/h steam from line (4), the feed mixture is completely evaporated in column (2) and withdrawn from the top of column (2). The temperature and the pressure in various lines are indicated in Table 2.

TABLE 2

|  | Example 1 | | Example 2 | |
|---|---|---|---|---|
| Line | Temperature (° C.) | Pressure (bar) | Temperature (° C.) | Pressure (bar) |
| 5 | 111 | 1.7 | 111 | 1.7 |
| 7 | 420 | 1.5 | 420 | 1.5 |
| 9 | 490 | 1.4 | 490 | 1.4 |
| 12 | 440 | 1.2 | 440 | 1.2 |
| 13 | 170 | 1.1 | 170 | 1.1 |
| 13a | 145 | 4.2 | 145 | 4.2 |
| 17 | 121 | 4.0 | 121 | 4.0 |
| 19 | 121 | 4.0 | 121 | 4.0 |
| 16 | 117 | 1.8 | 117 | 1.8 |
| 4 | 117 | 1.75 | 117 | 1.75 |
| 25 | — | — | 114 | 1.8 |

The power of the compressor (14) is 17 MW, for direct cooling water is injected into the mixture between the condensing steps. The product mixture withdrawn from line (19), the hydrocarbons of which still are vaporous, has the composition indicated in Table 3:

TABLE 3

|  |  | Example 1 | Example 2 |
|---|---|---|---|
| Propylene | (wt-%) | 16.3 | 12.8 |
| Ethylene | (wt-%) | 3.7 | 3.0 |
| Butene | (wt-%) | 12.2 | 9.4 |
| Olefins, $C_4$ to $C_8$ | (wt %) | 2.4 | 5.4 |
| Others | (wt %) | 44.4 | 48.4 |
| Steam | (wt-%) | 21.0 | 21.0 |

Due to the compression of the reaction products 95 MW heat can thus be provided and a cooling capacity of likewise about 95 MW, which is required for pressurizing the water content in the product mixture, can be saved in that 17 MW of pressurizing power are provided.

Example 2

The procedure is as shown in FIG. 2, and 100 000 kg/h of a feed mixture of 80° C. and the composition indicated in Table 1 (above) are supplied to column (2) through line (1). This feed mixture has a higher content of high-boiling components than the feed mixture of Example 1. Through line (4a) 33 000 kg/h of process steam are supplied, where 83 wt-% of the feed mixture are evaporated and are withdrawn from the top of column (2). The non-evaporated rest of the feed mixture is withdrawn through line (25) together with aqueous condensate. The hydrocarbons (16970 kg/h) withdrawn via line (28) have the composition indicated in Table 1, column A. The condensate withdrawn through line (27) is introduced into line (16) and thus recirculated to the condensate circuit. The hydrocarbon content of the mixture leaving column (2) at the top has the composition indicated in Table 1, column B. The ensuing process steps are analogous to those described in Example 1. The temperature and the pressure in the various lines are indicated in Table 2. 100000 kg/h steam are admixed to this mixture through line (4b), so that the steam content required in the reactor feed stream is achieved.

What is claimed is:

1. A process of producing $C_2$- to $C_4$-olefins from steam and a feed mixture containing $C_4$- to $C_8$-olefins, wherein the feed mixture containing steam is introduced into a reactor with an inlet temperature of 300 to 700° C., said reactor comprising a bed of granular, form selective zeolite catalyst, wherein a product mixture containing steam and $C_2$- to $C_4$-olefins is withdrawn from the bed and in passed through at least one cooling means, characterized in that the vaporous product mixture coming from the cooling means (6) is pressurized and the pressure of the product mixture is increased by 0.3 to 7 bar, that the pressurized product mixture is passed through an indirect heat exchanger (15) and the product mixture is cooled therein to such an extent that a water-rich condensate is produced by releasing heat of condensation, that the product mixture containing condensate is introduced into a separator from which a water-rich condensate and, separate therefrom, a vaporous product mixture containing $C_2$- to $C_4$-olefins is withdrawn that water-rich condensate coming from the separator is expanded and evaporated in the indirect heat exchanger by utilizing the heat of condensation previously released during condensation, that at last part of the steam is introduced from the indirect heat exchanger into a mixing chamber to which the feed mixture containing $C_4$- to $C_8$-olefins is supplied, and that a mixture containing steam is withdrawn from the mixture chamber, which mixture is heated and introduced into the reactor.

2. The process as claimed in claim 1, characterized in that the feed mixture supplied to the reactor contains steam and hydrocarbon in a weight ratio of 0.5:1 to 3:1.

3. The process as claimed in claim 1, characterized in that the product mixture coming from the cooling means (6) has a temperature of 60 to 200° C. and a pressure of 0.5 to 3 bar and is still vaporous.

4. The process as claimed in claim 1, characterized in that the feed mixture supplied to the mixing chamber contains hydrocarbons with more than 8 C-atoms per molecule, that the mixing chamber is designed as column with a gas- and liquid-permeable packing, that the feed mixture is supplied onto the upper portion of the packing, and $C_4$- to $C_8$-olefins from the feed mixture are evaporated with a partial amount of the steam supplied to the column in the lower portion of the packing and are withdrawn from the column together with the steam.

5. The process as claimed in claim 4, characterized in that a liquid mixture containing water and hydrocarbons is withdrawn from the column, from which liquid mixture water is separated which is added to the expanded water-rich condensate before reaching the indirect heat exchanger.

* * * * *

UNITED STATES PATENT AND TRADEMARK OFFICE
CERTIFICATE OF CORRECTION

PATENT NO. : 6,953,872 B1 Page 1 of 1
APPLICATION NO. : 10/030802
DATED : October 11, 2005
INVENTOR(S) : Koss et al.

It is certified that error appears in the above-identified patent and that said Letters Patent is hereby corrected as shown below:

Column 3, Line 42, "CB" should read -- $C_8$ --

Column 3, Line 53, Table 1, "$C_4$- to $C_5$-olefins" should read -- $C_4$- to $C_8$-olefins --

Column 3, Line 56, Table 1, "38.0  13.0" should read -- 38.0  19.0 --

Column 3, Line 58, Table 1, "Aromatics ($c_{8+}$)" should read -- Aromatics ($C_{8+}$) --

Column 5, Line 1, "form selective" should read -- form-selective --

Column 5, Line 3, "and in passed through" should read -- and is passed through --

Column 5, Line 14, 'withdrawn that" should read -- withdrawn, that --

Column 5, Line 18, "that at last part" should read -- that at least part --

Column 5, Line 22, "mixture chamber" should read -- mixing chamber --

Column 6, Line 3, "hydrocarbon" should read -- hydrocarbons --

Signed and Sealed this

Fourth Day of September, 2007

JON W. DUDAS
*Director of the United States Patent and Trademark Office*